(12) United States Patent
Zhang et al.

(10) Patent No.: US 12,049,635 B2
(45) Date of Patent: Jul. 30, 2024

(54) TRANSGENIC METHOD OF OBTAINING BLUE FLOWERS BY CATALYZING GLUTAMINE TO SYNTHESIZE INDIGO

(71) Applicants: TIANJIN UNIVERSITY, Tianjin (CN); Institute of Microbiology Chinese Academy of Sciences, Beijing (CN)

(72) Inventors: Yan Zhang, Tianjin (CN); Yihua Chen, Beijing (CN); Nanjaraj Urs Ankanahalli, Tianjin (CN); Yiling Hu, Tianjin (CN); Pengwei Li, Beijing (CN)

(73) Assignees: TIANJIN UNIVERSITY, Tianjin (CN); Institute of Microbiology Chinese Academy of Sciences, Beijing (CN)

( * ) Notice: Subject to any disclaimer, the term of this patent is extended or adjusted under 35 U.S.C. 154(b) by 944 days.

(21) Appl. No.: 16/966,719

(22) PCT Filed: Nov. 23, 2018

(86) PCT No.: PCT/CN2018/117160
§ 371 (c)(1),
(2) Date: Jul. 31, 2020

(87) PCT Pub. No.: WO2019/148944
PCT Pub. Date: Aug. 8, 2019

(65) Prior Publication Data
US 2023/0257760 A1 Aug. 17, 2023

(30) Foreign Application Priority Data
Jan. 31, 2018 (CN) .......................... 201810095829.2

(51) Int. Cl.
C12N 15/82 (2006.01)
C12N 9/12 (2006.01)
C12N 9/88 (2006.01)

(52) U.S. Cl.
CPC ......... *C12N 15/825* (2013.01); *C12N 9/1288* (2013.01); *C12N 9/88* (2013.01); *C12N 15/8205* (2013.01); *C12Y 207/08007* (2013.01)

(58) Field of Classification Search
None
See application file for complete search history.

(56) References Cited

U.S. PATENT DOCUMENTS

| 6,268,546 | B1 | 7/2001 | McBride et al. |
| 10,741,191 | B2 * | 8/2020 | Kim .......................... G10L 25/78 |
| 2001/0014977 | A1 | 8/2001 | McBride et al. |
| 2011/0023162 | A1 | 1/2011 | Brugliera |
| 2011/0126320 | A1 | 5/2011 | Tanaka et al. |
| 2011/0191907 | A1 | 8/2011 | Yuki et al. |
| 2015/0074856 | A1 | 3/2015 | Brugliera |
| 2016/0168619 | A1 * | 6/2016 | Tao ..................... G01N 33/6812 702/19 |
| 2016/0299151 | A1 * | 10/2016 | Ackerley ................. C12Q 1/48 |

FOREIGN PATENT DOCUMENTS

| CN | 1189856 A | 8/1998 |
| CN | 1970642 A | 5/2007 |
| CN | 108330146 A | 7/2018 |
| JP | 2007189969 A | 8/2007 |
| JP | 2013055955 A | 3/2013 |
| WO | WO 96/40951 A2 | 12/1996 |
| WO | 2005017147 A1 | 5/2005 |
| WO | 2009062253 A1 | 5/2009 |

OTHER PUBLICATIONS

Genbank accession KT429820. "Low temperature-induced DNA hypermethylation attenuates expression of RhAG, an AGAMOUS homolog, and increases petal number in rose (Rosa hybrida)." Ma et al. BMC Plant Biology. 15(1), 237. (Year: 2015).*
GenBank accessoin KY381898. Xie et al. "Synthetic construct clone T5-RBSs-midgS, complete sequence." Applied Microbiology and Biotechnology. (Year: 2017).*
Vickery et al. "Dissecting modular synthases through inhibition: A complementary chemical and genetic approach". Bioorganic & Medicinal Chemistry Letters. 30(2). (Year: 2020).*
Ma, N. et al.; "Rosa hybrid cultivar Vendela AGAMOUS-like protein (RhAg) gene, promoter region and 5' UTR"; BMC Plant Biol. 15 (1), p. 237; Oct. 20, 2015 (1 page).
Hitoshi Takahashi et al.; "Cloning and Characterization of a Streptomyces Single Module Type Non-ribosomal Peptide Synthetase Catalyzing a Blue Pigment Synthesis"; Journal of Biological Chemistry, vol. 282, No. 12, pp. 9073-9081; Mar. 23, 2007 (originally published online Jan. 19, 2007; DOI: 10.1074/jbc.M611319200 (10 pages).

(Continued)

Primary Examiner — Mykola V. Kovalenko
Assistant Examiner — David R Byrnes
(74) Attorney, Agent, or Firm — NIXON PEABODY LP; David S. Resnick; Bradley M. Taub

(57) ABSTRACT

A transgenic method of obtaining blue flowers by catalyzing glutamine to synthesize indigo. The steps include: 1) respectively cloning a Sfp gene encoding phosphopantetheinyl transferase and a bpsA gene encoding indigo synthase downstream of a plant promoter in a plant-promoter-containing plasmid; 2) amplifying the obtained plasmid in *E. coli* and then transferring the same to *Agrobacterium tumefaciens*; and 3) transferring DNA containing Sfp and bpsA into a plant. The blue flowers produced by the present invention have various characteristics of natural flowers, being fresh, flower-scented, non-color-fading, and non-toxic. The transgene-encoded enzyme and the produced indigo are not in the vacuole and are not affected by the low pH of the plant vacuole, thereby resulting in a pure blue color. The precursor of the blue matter, i.e., the substrate of the enzyme, is glutamine, which is abundant in plants. The enzyme catalysis reaction comprises a single step, and the transgenic transformation can be carried out on natural white flowers.

13 Claims, 3 Drawing Sheets
Specification includes a Sequence Listing.

(56) References Cited

OTHER PUBLICATIONS

Ankanahalli N. Nanjaraj Urs et al.; "Cloning and expression of a non-ribosomal peptide synthetase to generate blue rose"; ACS Synth. Biol.; Sep. 14, 2018; DOI: 10.1021/acssynbio.8b00187; downloaded from http://pubs.acs.org on Sep. 16, 2018 (18 pages).
Owen, J. G. et al.; "A functional screen for recovery of 4'-phosphopantetheinyl transferase and associated natural product biosynthesis genes from metagenome libraries"; Environmental Microbiology (2012), vol. 14, No. 5, pp. 1198-1209 ; DOI: 10.1111/j.1462-2920.2012.02699.x; Jan. 6, 2012 (12 pages).
Ma, N. et al.; "Low temperature-induced DNA hypermethylation attenuates expression of RhAG, an AGAMOUS homolog, and increases petal number in rose (Rosa hybrida)"; BMC Plant Biology (2015), vol. 15, No. 237; Oct. 15, 2015; DOI 10.1186/s12870-015-0623-1 (13 pages).
Mason, J. et al.; "Flavonoid 3',5' Hydroxylase gene sequences and uses therefor"; Patent: JP 2010193895-A; International Flower Developments Pty Ltd.; Sep. 9, 2010 (1 page).
Ma, N. et al.; "Rosa hybrid cultivar Vendela AGAMOUS-like protein (RhAG) gene, promoter region and 5'UTR"; BMC Plant Biol. 15 (1), 237 (2015); Oct. 20, 2015 (2 pages).
Dao, T. T. H. et al.; "Chalcone synthase and its functions in plant resistance"; Phytochem. Rev. (2011) No. 10, pp. 397-412; May 3, 2011; DOI 10.1007/s11101-011-9211-7 (16 pages).
European Patent Office; European Search Opinion for Application No. 18903578, dated Oct. 29, 2021 (5 pages).
Muller, M. et al.; "A novel reporter system for bacterial and mammalian cells based on the non-ribosomal peptide indigoidine"; Metabolic Engineering 14.4(2012):325-335, XP028429533, ISSN: 1096-7176, DOI: 10.1016/J.YMBEN.2012.04.002 (11 pages).
European Patent Office; Supplementary European Search Report for Application No. 18903578, dated Oct. 29, 2021 (2 pages).
Database GenBank [Online] Apr. 6, 2020 (Apr. 6, 2020), Database accession No. ACK77757 Quadri et al. "Characterization of Sfp, a Bacillus subtilis phosphopantetheinyl transferase for peptidyi carrier protein domains in peptide synthetases." Biochemistry 37.6 (1998): 1585-1595.
Novakova et al. "Identification and characterization of an indigoidine-like gene for a blue pigment biosynthesis in Streptomyces aureofaciens CCM 3239." Folia microbiologica 55 (2010): 119-125.
Office Action dated Apr. 13, 2023, issued by the European Patent Office for European Patent Application No. 18 903 578.5-1118.
Quadri et al. "Characterization of Sfp, a Bacillus subtilis phosphopantetheinyl transferase for peptidyl carrier protein domains in peptide synthetases." Biochemistry 37.6 (1998): 1585-1595.
Zhoujie Xie et al.; "An external substrate-free blue/white screening system in *Escherichia coli*"; Appl.Microbiol. Biotechnol., 101(9), pp. 3811-3820; Mar. 28, 2017; DOI: 10.1007/s00253-017-8252-2 (11 pages).
Liu, M. et al.; "Database Genbank [online], Accession No. CP013654, Definition: *Bacillus subtilis* subsp. *subtilis* strain BSD-2 chromosome, complete genome"; Dec. 14, 2015; retrieved from the Internet: http://www.ncbi.nlm.nih.gov/huccore/CP013654.1?from=3214119&report=gbwithparts (3 pages).
Holton, T.A. & Tanaka, Y., "Blue roses: a pigment of our imagination?," Trends in Biotechnology, 12(2): 40-42 (1994).
Mikanagi, Y. et al., "Anthocyanins in flowers of genus *Rosa*, sections Cinnamomeae (=Rosa), Chinenses, Gallicanae and some modern garden roses," Biochemical Systematics & Ecology, 28(9): 887 (2000).
Grotewold, E., "The genetics and biochemistry of floral pigments," Annual Review of Plant Biology, 57(1):761 (2006).
Katsumoto, Y. et al., "Engineering of the rose flavonoid biosynthetic pathway successfully generated blue-hued flowers accumulating delphinidin," Plant & Cell Physiology, 48(11): 1589 (2007).
PhysOrg, "Blue roses to debut in Japan," Web Page, <https://phys.org/news/2009-10-blue-roses-debut-japan.html>, Retrieved from the Internet Aug. 30, 2012 (2 pages).
Tanaka, Y. & Brugliera, F., "Flower colour and cytochromes P450," Philosophical Transactions of the Royal Society of London, 368(1612): 283-291(2013).
Takahashi, H. et al., "Cloning and Characterization of a Streptomyces Single Module Type Nonribosomal Peptide Synthetase Catalyzing a Blue Pigment Synthesis," Journal of Biological Chemistry, vol. 28, No. 12 (Jan. 19, 2017).
Nanjaraj Urs, A.N. et al., "Cloning and Expression of a Nonribosomal Peptide Synthetase to Generate Blue Rose," ACS Synthetic Biology, vol. 7, No. 9 (Sep. 14, 2018).
International Search Report in International Application No. PCT/CN2018/117160, mailed Feb. 14, 2019 (8 pages).
Database GenBank [Online] Oct. 20, 2015, Database accession No. KT429820 Ma, N. et al.; "Rosa hybrid cultivar Vendela AGAMOUS-like protein (RhAG) gene, promoter region and 5' UTR"; BMC Plant Biol. 15(1), 237; Oct. 20, 2015 (2 pages).
Database GenBank [Online] Jun. 20, 2019, Database accession No. WP_030237949 Konz, D. et al.; "Amino acid adenylation domain-containing protein [Streptomyces lavendulae]"; Chem. Biol. 6 (2), R39-R48; Jun. 20, 2019 (2 pages).
Database GenBank [Online] Feb. 24, 2005, Database accession No. DD118139 Mizutani, M. et al.; "Process for production of rose with altered color"; Patent: WO 2005017147-A; Feb. 24, 2005 (2 pages).
Database GenBank [Online] Jul. 10, 2019, Database accession No. WP_069322372 Reuter, K. et al.; "4'-phosphopantetheinyl transferase [Bacillus subtilis]"; Embo J. 18 (23), 6823-6831; Jul. 10, 2019 (2 pages).

\* cited by examiner

TRANSGENIC METHOD OF OBTAINING BLUE FLOWERS BY CATALYZING GLUTAMINE TO SYNTHESIZE INDIGO

CROSS-REFERENCE TO RELATED APPLICATIONS

This application is a U.S. National Stage of International Application Patent No. PCT/CN2018/117160, filed on Nov. 23, 2018, which claims the benefit of and priority to Chinese Patent Application No. 201810095829.2, filed on Jan. 31, 2018, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Oct. 4, 2020, is named 078291-000211US-PX_SL.txt and is 32,071 bytes in size.

TECHNICAL FIELD

The invention belongs to the field of biotechnology, and relates to a transgenic method of obtaining a plant with blue flowers by catalyzing synthesis from glutamine to indigoidine.

BACKGROUND TO THE INVENTION

Flower color is an important ornamental feature of ornamental plants, and improvement in flower color has always been one of the important goals of gardeners. The color of flowers not only plays an important role in the pollination and reproduction of plants, but also provides a colorful viewing experience for humans, and thus has important aesthetic value (Grotewold, E. The genetics and biochemistry of floral Pigments [J]. Annual Review of Plant Biology, 2006, 57(1): 761). As an important ornamental plant, modern rose (Rosa hybrida) has been cultivated for 5000 years. So far, more than 2,500 varieties have cultivated, but there are no true blue roses among them.

Actually, the existing blue roses on the market, such as "Blue Fairy", are dyed blue with dyes (Holton T. A, Tanaka Y. Blue roses: a pigment of our imagination? [J]. Trends in Biotechnology: United Kingdom, 1994, 12(2): 40-42). Blue rose as an idiom in English means a miracle that would never come true. It frequently appears in various literary and artistic works including movies, TV, poetry, novels, dramas and the like.

The flower color of a plant is determined by many factors, including flavonoids such as anthocyanins, terpenes such as carotene, as well as pH of vacuole and metal ions, etc. (Tanaka Y, Brugliera F. Flower colour and cytochromes P450 [J]. Philosophical Transactions of the Royal Society of London, 2013, 368 (1612): 283-291). The hydroxylation of anthocyanins at different positions and different degrees makes the flowers have different colors, in which the flavonoid 3'5' hydroxylase (F3'5'H) catalyzes the formation of delphinidin, which leads to blue flowers for many plants. Since many plants including roses lack the gene encoding F3'5'H, such plants do not have blue flowers (Mikanagi Y, Saito N, Yokoi M, et al. Anthocyanins in flowers of genus Rosa, sections Cinnamomeae (=Rosa), Chinenses, Gallicanae and some modern garden roses [J]. Biochemical Systematics & Ecology, 2000, 28(9): 887).

Suntory Corp. from Japan used transgenic technology to make plants that cannot bloom blue flowers in nature bloom blue flowers by introducing foreign genes including F3'5'H and simultaneously suppressing the expression of several other genes. This method involves the modifications to multiple genes, and requires complex precursor materials, and therefore the cost is expensive. This technology has been successful in carnations and chrysanthemums. Since the pH of vacuole in roses is very low (about 2.7), this technology can only obtain lilac flowers for roses, and cannot show the true blue color (FIG. 1) (Katsumoto Y, Fukuchimizutani M, Fukui Y, et al. Engineering of the rose flavonoid biosynthetic pathway successfully generated blue-hued flowers accumulating delphinidin. [J]. Plant & Cell Physiology, 2007, 48(11): 1589). Nonetheless, each of the lilac roses costs 22-35 US dollars (Staff (20 Oct. 2009). "Blue roses to debut in Japan". The Independent, House and Home. Retrieved 30 Aug. 2012), and it brings huge economic benefits to Suntory. Currently, the roses are only available in Japan and the American continent. The acquisition of true blue roses is still a technical problem that has not be solved yet.

SUMMARY OF THE INVENTION

The purpose of the present invention is to overcome the deficiencies of the prior art and provides a transgenic method of obtaining a plant with blue flowers by catalyzing synthesis from glutamine to indigoidine.

The technical solution of the present invention is summarized as follows:

A transgenic method of obtaining a plant with a blue flower by catalyzing synthesis from glutamine to indigoidine includes the following steps:
1) selecting a Sfp gene encoding phosphopantetheinyl transferase and a bpsA gene encoding indigoidine synthetase, and cloning the two genes downstream a plant promoter of a plasmid containing the plant promoter, respectively;
2) amplifying the plasmid obtained in step 1) in *Escherichia coli* and transforming the amplified plasmid into *Agrobacterium tumefaciens*;
3) transfecting Sfp and bpsA DNA into the plant by *Agrobacterium*-mediated transfection;
4) allowing Sfp and BpsA proteins to be functionally expressed in a petal cell, thereby turning a petal blue via synthesis from glutamine to indigoidine;
wherein the Sfp gene is a gene derived from any species that encodes phosphopantetheinyl transferase, or a gene that encodes an isoenzyme of phosphopantetheinyl transferase; and
the bpsA gene is a gene derived from any species that encodes indigoidine synthetase, or a gene that encodes an isoenzyme of indigoidine synthetase;

The plant promoter is a DNA sequence that can drive downstream gene expression in plant cells.

Preferably, the Sfp gene has the nucleotide sequence as shown in SEQ ID NO.1.

Preferably, the phosphopantetheinyl transferase encoded by the Sfp gene has the amino acid sequence as shown in SEQ ID NO. 2.

Preferably, the bpsA gene has the nucleotide sequence as shown in SEQ ID NO. 3.

Preferably, the indigoidine synthetase encoded by the bpsA gene has the amino acid sequence as shown in SEQ ID NO. 4.

Preferably, a plant promoter CHSp having the nucleotide sequence as shown in SEQ ID NO. 5 is upstream the Sfp gene.

Preferably, a plant promoter RhAGp having the nucleotide sequence as shown in SEQ ID NO. 6 is upstream the bpsA gene.

Preferably, the plasmid containing the plant promoter is pBI121.

The plant is rose, rosa chinensis, lily, chrysanthemum, carnation or orchid.

A transgenic method of obtaining a plant with a blue flower, comprising rendering a petal of the plant to contain indigoidine, wherein the plant is rose, rosa chinensis, lily, chrysanthemum, carnation, or orchid.

The advantages of the invention:

The present invention overcomes the deficiencies of the prior art such as dyeing method and transgenic method. The dyeing of flowers has more obvious artificial traces and is easy to decolor. The organic dyes used are usually poisonous. Usually, flowers are dried flowers and do not have the fragrance of flowers. If fresh flowers are dyed, they would not be easily preserved, and become withered soon. The blue flowers produced by the method of the present invention have numerous characteristics of natural flowers: fresh, floral, non-fading and non-toxic.

The enzymes encoded by the genes used in the method of the present invention are not present in the vacuole and the indigoidine produced is not present in the vacuole either, it therefore is not affected by the low pH of the vacuole and can form a pure blue (royal blue). The precursor that produces blue substance, i.e. the substrate of the enzyme, is a simple amino acid (glutamine) rich in plants, and the enzymatic reaction involved is just one step, and does not need complex precursor materials. The white flowers in nature, as a starting material, can be geneticaly modified.

The plants with blue flowers, such as lily, rosa chinensis, chrysanthemum, carnation, orchid and the like, in particular blue roses, are obtained by the transgenic methods.

BRIEF DESCRIPTION OF DRAWINGS

FIG. 1-1 is Suntory's genetic modification flow diagram for obtaining lilac roses through the biosynthesis of delphinidin; FIG. 1-2 is a photo of the lilac roses finally obtained by Suntory.

FIG. 2: Information diagram of phosphopantetheinyl transferase Sfp and indigoidine synthetase bpsA, which includes the schematic diagram of the reaction process of phosphopantetheinyl transferase (FIG. 2-1), the structure and reaction mechanism of the encoding indigoidine synthetase bpsA (FIG. 2-2), the SDS-PAGE electropherogram of indigoidine synthetase bpsA (FIG. 2-3) and the absorption spectrum of the blue compound indigoidine (FIG. 2-4).

FIG. 4-1 shows the transfected blue petals; the left side of FIG. 4-2 is the negative control without acetosyringone and the right side of FIG. 4-2 is the blue rose petals obtained after addition of acetosyringone and transient transfection; the arrow indicates the position for transient transfection, and the dashed circle shows the blue spot area.

MODES FOR CARRYING OUT THE INVENTION

A phosphopantetheinyl transferase is used in the invention to activate indigoidine synthetase, and the activated indigoidine synthetase catalyzes glutamine to synthesize blue compound indigoidine which turns the white roses blue. The invention uses modern roses (*Rosa hybrida*) as an example, but the plants with blue flowers obtained by the method are not limited to modern roses. Experiments shows that rose, rosa chinensis, lily, chrysanthemum, carnation or orchid with blue flowers can be obtained by the method of the present invention. In an embodiment, the transfection method for plant cell may be a process of introducing artificially modified gene sequences into plant cells by physical, chemical, or biological means. A biological means, i.e. *Agrobacterium tumefaciens*-mediated transfection method for plant cells is used in the present invention.

The present invention will be further described below in combination with specific examples.

EXAMPLE 1

Selection of Gene

Figure 1:
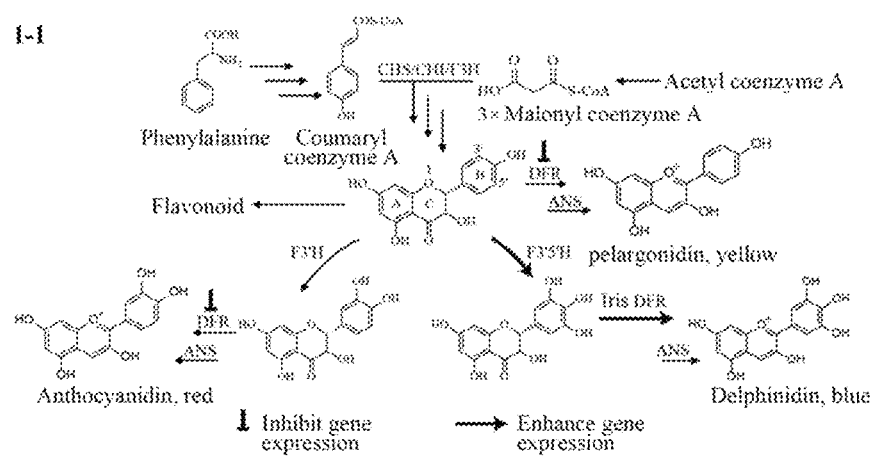
FIG. 1: Modification strategy for Suntory (Japan) to obtain a blue rose.
Figure 1:
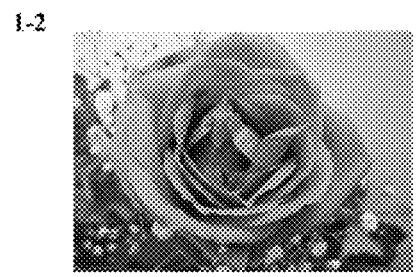
Figure 2:
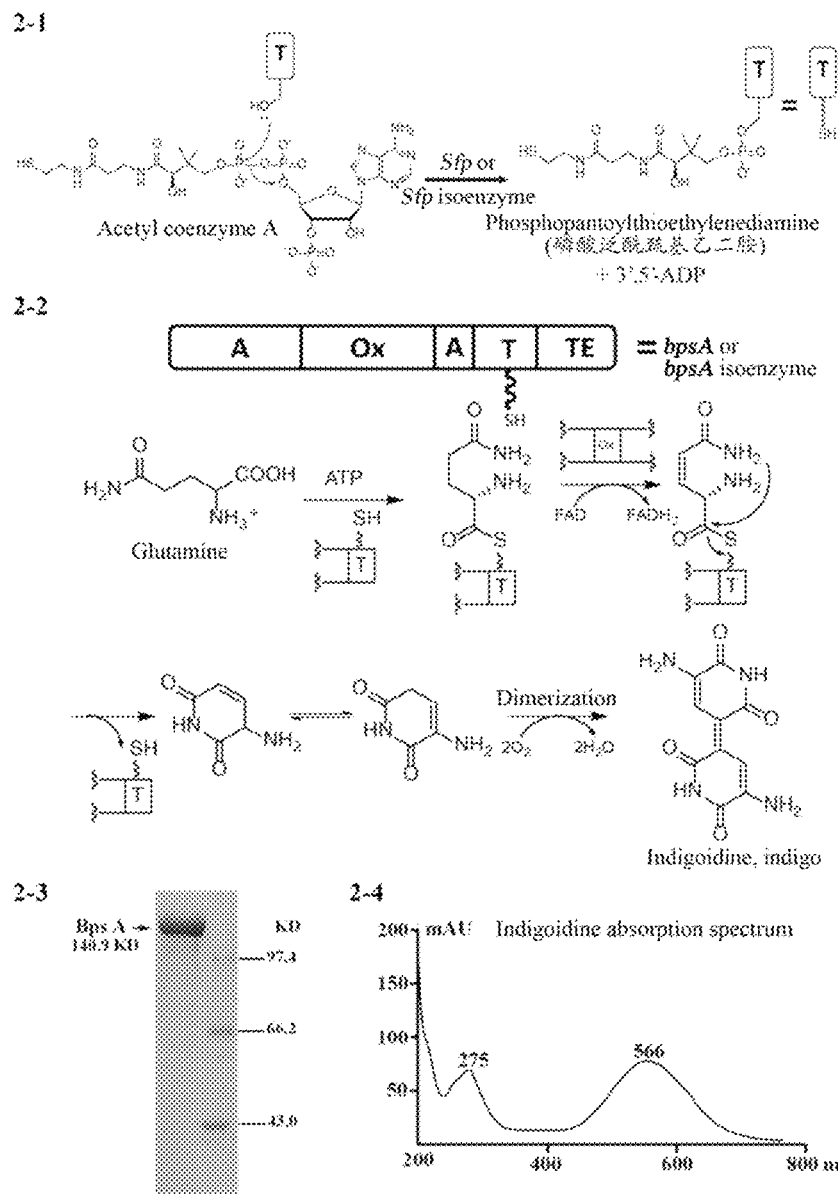

Phosphopantetheinyl transferase activates the thiolated domain T of the non-ribosomal polypeptide synthetase and the reaction mechanism is shown in FIG. 2-1. The activated T domain functions to fix the substrate, and this function is necessary for the catalytic function of the non-ribosomal polypeptide synthetase.

The Sfp gene of phosphopantetheinyl transferase used in the present invention was derived from *Bacillus subtilis* ATCC 21332 (NCBI No.: ALS83446). The gene codons were optimized according to the gene codon preference of Rosaceae plants to obtain the nucleotide sequence of SEQ ID NO. 1. The amino acid sequence encoded by the Sfp gene was shown in SEQ ID NO. 2. The selection of the Sfp gene should not be limited to the phosphopantetheinyl transferase used in the present invention. The method of using any genes encoding phosphopantetheinyl transferase derived from other species, or any genes encoding an isoenzyme of phosphopantetheinyl transferase together with the indigoidine synthetase to obtain the blue flowers should fall into the protection scope of the present invention.

Figure 3:
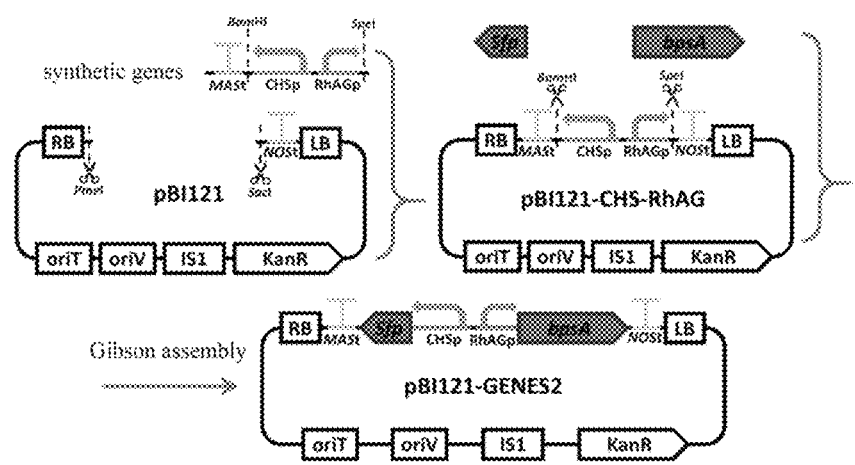
FIG. 3: Schematic diagram for constructing the expression plasmid pBI121-GENES2, in which oriT: transfer initiation region, gene transfer element; oriV: plasmid replication initiation region; IS1: gene transposition element; KanR: kanamycin resistance gene; LB/RB: repeat sequences from nopaline C58T-DNA, gene transposition element; MASt/NOSt: terminator; CHSp: Chalcone Synthase gene promoter; RhAGp: a promoter of a gene encoding AGAMOUS-like protein.
Figure 4:
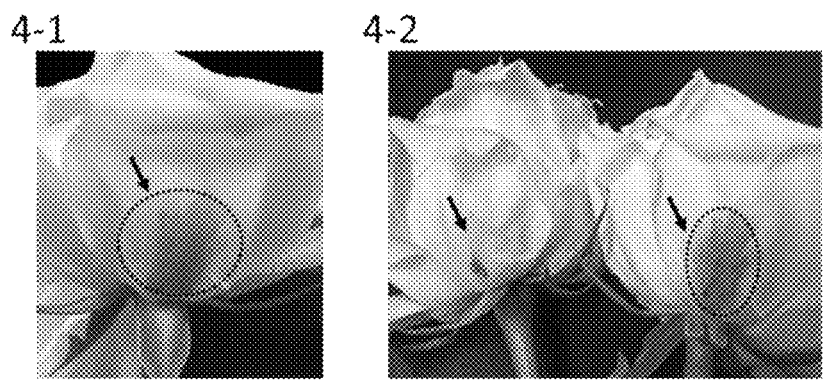
FIG. 4: Graph of blue petals obtained by transient transfection of roses with bpsA mediated by *Agrobacterium tumefaciens*.

Indigoidine synthetase, a non-ribosomal polypeptide synthetase, contains two amino acid-specific recognition domains A, an oxidation domain Ox containing flavin (FMN), a thiolation domain T, and a domain TE responsible for product dissociation. Indigoidine synthetase functions to catalyze synthesis from two molecules of glutamine to the blue compound indigoidine. The mechanism is shown in FIG. 2-2. The molecular formula of the formed indigoidine is shown in FIG. 2-2, and the absorption spectrum is shown in FIG. 2-4. Compared with other dyes, the formed indigoidine has good solubility and blue gloss, and has no obvious damage to plant cells.

The bpsA gene encoding indigoidine synthetase selected by the present invention was derived from *Streptomyces lavendulae* ATCC11924. The amino acid sequence encoded by bpsA was shown in SEQ ID NO.4 (NCBI No.: WP_030237949). The gene codons were optimized according to the gene codon preference of Rosaceae plants to obtain the nucleotide sequence of SEQ ID NO. 3. The full length of the bpsA gene encoding indigoidine synthetase was 3846 bases, and the encoded protein was 1282 amino acids and approximately 140 KD. The purified protein on SDS-PAGE was shown in FIG. 2-3. The selection of the bpsA gene should not be limited to the indigoidine synthetase used in the present invention. The method of using any genes encoding indigoidine synthetase derived from other species, or any genes encoding an isoenzyme of indigoidine synthetase together with the phosphopantetheinyl transferase to obtain the blue flowers should fall into the protection scope of the present invention.

The sequences of the plant promoters CHSp promoter and RhAGp promoter derived from rose (*Rosa hybrida*) are shown in SEQ ID NO. 5 (NCBI No.: FW556946) and SEQ ID NO. 6 (NCBI No.: U43372), respectively.

EXAMPLE 2

Plasmid Cloning

In the present invention, the plant binary expression vector pBI121 was selected as the starting plasmid vector.

A synthetic fragment (SEQ ID NO. 7) was inserted between the restriction sites PmeI and SacI of the plasmid pBI121 to construct plasmid pBI121-CHS-RhAG, as shown in FIG. 3. SEQ ID NO. 7 included the terminator sequence MASt of mannopine synthase, the promoter sequence CHSp and the promoter sequence RhAGp.

The fragment bpsA was obtained by PCR of using the plasmid containing the sequence of SEQ ID NO. 3 as a template and BpsA-FG (SEQ ID NO. 8) and BpsA-RG (SEQ ID NO. 9) as primers.

The fragment Sfp was obtained by PCR of using the plasmid containing the sequence of SEQ ID NO. 1 as a template, and Sfp-FG (SEQ ID NO. 10) and Sfp-RG (SEQ ID NO. 11) as primers.

Plasmid pBI121-CHS-RhAG was digested with restriction enzymes BamHI and SpeI. After purification and recovery, fragment CHS-RhAG and plasmid framework pBI121 were obtained. The reaction was carried out at 50° C. for 1 hour by using NEBuilder® HiFi DNA Assembly Master Mix (New England Biolabs, USA) system, and the product was transformed into *E. coli* competent cells to obtain clones and the clones were amplified. After sequencing to conform the correct sequence, the binary expression plasmid pBI121-GENES2 was obtained, as shown in FIG. 3.

EXAMPLE 3

Preparation of Competent Cells of *Agrobacterium tumefaciens* with the Target Gene The plasmid pBI121-GENES2 obtained by plasmid extraction of *E. coli* was transformed into *Agrobacterium tumefaciens*. The competent cells of *Agrobacterium tumefaciens* was prepared by the following common method:
 1. *Agrobacterium tumefaciens* (*Agrobacterium tumefaciens* GV3101) was cultured on LB agar medium containing 10 μg/mL rifampicin and 50 μg/mL gentamicin at 28° C. for two days;
 2. The monoclonal colony was cultured in 5 mL of LB liquid culture medium containing the same antibiotics (10 μg/mL rifampicin and 50 μg/mL gentamicin), and cultured on a shaker (150 rpm) at 28° C. overnight.
 3. 2 mL of *Agrobacterium tumefaciens* culture solution cultured overnight was diluted to 200 mL of LB culture medium, and cultured on a shaker (250 rpm) at 28° C. to OD600 of 0.3 to 0.5.
 4. The *Agrobacterium tumefaciens* culture solution was filled in a 50 mL centrifuge tube, cooled on ice, and centrifuged at 3000×g.
 5. After removing the supernatant, *Agrobacterium tumefaciens* cells were resuspended in 80 mL of CCMB80 buffer precooled on ice and placed on ice to cool for 20 minutes. The formula of CCMB80 buffer was as follows: 10 mM potassium acetate, 80 mM $CaCl_2 \cdot 2H_2O$, 20 mM $MnCl_2 \cdot 4H_2O$, 10 mM $MgCl_2 \cdot 6H_2O$, and 10% glycerol, pH 6.4.
 6. The cells were centrifuged again, and resuspended in 5 mL of precooled CCMB80 buffer after removing the supernatant.
 7. The cells were dispensed into 1.5 mL EP tubes with 100 μL per tube, and frozen with liquid nitrogen, and stored in a refrigerator at −80° C.

The transformation of *Agrobacterium tumefaciens* was as follows:
 1) 1 μg of plasmid DNA (pBI121-GENES2) was added to 100 μL of the competent cell suspension of *Agrobacterium tumefaciens* prepared as above on ice, and the cells were frozen with liquid nitrogen.
 2) The competent cells of *Agrobacterium tumefaciens* containing the plasmid DNA were thawed in a water bath at 37° C. for 5 min.
 3) 1 mL of antibiotic-free LB culture medium was added and cultured on a shaker (150 rpm) at 28° C. for 3 hours.
 4) The culture was centrifuged at a low speed to obtain cells.
 5) The cells was spread on an LB agar plate, and placed in an incubator at 28° C., and selected with antibiotics to obtain the colonies containing resistance gene. The LB agar contained 10 μg/mL of rifampicin, 50 μg/mL of gentamicin and 50 μg/mL of kanamycin.
 6) Colony growth could be seen in two to three days.

EXAMPLE 4

Transgenic Blue Roses Obtained by Transient Transfection of bpsA Mediated by *Agrobacterium tumefaciens*
 1. The successfully transformed *Agrobacterium tumefaciens* GV3101 colony was added into 5 mL of LB culture medium containing antibiotics (10 μg/mL of rifampicin, 50 μg/mL of gentamicin and 50 μg/mL of kanamycin), and cultured at 28° C. on a shaker (200 rpm) overnight.
 2. 1 mL of the *Agrobacterium tumefaciens* solution obtained from step 1 was added into 100 mL of LB culture medium containing the same antibiotics, and cultured at 28° C. at 200 RPM until OD600 reached 1.5.
 3. The *Agrobacterium tumefaciens* cells were centrifuged at 3000×g for 10 minutes to remove the supernatant, and suspended in the buffers containing 10 mM $MgCl_2$, 10 mM MES (pH 5.6) (negative control) or the same buffer with additional 150 μg/mL of acetosyringone (positive control) to the cell density OD600 in the range of 0.5-1.0, and stored at room temperature for 3-5 hours in the dark.
 4. The whole flower branch of fresh white rose (*Rosa hybrida*) was selected and the stem was immersed into sterile water.
 5. The veins on the petals were marked on the back of the petals to avoid tissue damage.
 6. 100-150 μL of the *Agrobacterium tumefaciens* cell suspension containing acetosyringone (positive control) and without acetosyringone (negative control) obtained from step 3 were slowly injected into the main vein by using a disposable needle syringe of 1 mL, and the flower branch were stored at 22° C. in the dark for more than 12 hours.

The experimental results are shown in FIG. 4. The arrow indicates the position for transient transfection, and the dashed circle shows the blue spot area. FIG. 4-1 shows the transfected blue petals. The flower on the left of FIG. 4-2 is transfected by the competent cells of *Agrobacterium tumefaciens* with the same cell density without acetosyringone. The *Agrobacterium tumefaciens* cells are located in situ of injection and in the vicinity of transvenous transfer. The flower on the right of FIG. 4-2 is the flower that successfully transfect genes and make petals blue in the presence of acetosyringone that stimulates gene transfection from *Agrobacterium tumefaciens* into plant cells.

The experimental results show that bpsA derived from *Streptomyces* and Sfp derived from *Bacillus subtilisgenes* are transfected into the cells of the roses via *Agrobacterium tumefaciens*-mediated transfection, and the corresponding active non-ribosomal polypeptide synthetases are expressed in the plant cells. The synthetases synthesize blue indigoidine by using glutamine in the plant cells, thereby turning the rose petals blue.

---

What is claimed is:

1. A transgenic method of obtaining a plant with a blue flower by catalyzing synthesis from glutamine to indigoidine comprising:
   transfecting a Sfp gene encoding phosphopantetheinyl transferase and a bpsA gene encoding indigoidine synthetase into the plant to allow Sfp and BpsA proteins to be functionally expressed in a petal cell of the plant, thereby turning a petal blue via synthesis from glutamine to indigoidine;
   wherein the Sfp gene is a gene that encodes phosphopantetheinyl transferase having the amino acid sequence of SEQ ID NO:2; and
   the bpsA gene is a gene that encodes indigoidine synthetase having the amino acid sequence of SEQ ID NO: 4; and the plant is a rose.

2. The method of claim 1, wherein the Sfp gene has the nucleotide sequence as shown in SEQ ID NO. 1.

3. The method of claim 1, wherein the bpsA gene has the nucleotide sequence as shown in SEQ ID NO. 3.

4. The method of claim 1, wherein the Sfp gene encoding the phosphopantetheinyl transferase and the bpsA gene encoding indigoidine synthetase are respectively cloned into a plasmid.

5. The method of claim 4, wherein the plasmid contains plant promoters, and the Sfp gene and the bpsA gene are cloned downstream one of the plant promoters, respectively.

6. The method of claim 5, wherein the plant promoter upstream the Sfp gene is CHSp, which has the nucleotide sequence as shown in SEQ ID NO. 5.

7. The method of claim 5, wherein the plant promoter upstream the bpsA gene is RhAGp, which has the nucleotide sequence as shown in SEQ ID NO. 6.

8. The method of claim 1, wherein the transfecting steps result in that the Sfp gene encoding the phosphopantetheinyl transferase and the bpsA gene encoding indigoidine synthetase are integrated into the genome of the plant.

9. The method of claim 4, wherein the plasmid is amplified in *Escherichia coli* and the amplified plasmid is transformed into *Agrobacterium tumefaciens*.

10. The method of claim 1, wherein the Sfp gene and the bpsA gene are transfected into the plant based on *Agrobacterium*-mediated transfection.

11. A plant, which is transiently or stably transfected with a Sfp gene encoding phosphopantetheinyl transferase and a bpsA gene encoding indigoidine synthetase, such that a phosphopantetheinyl transferase encoded by the Sfp gene and indigoidine synthetase encoded by the bpsA gene are functionally expressed in a petal cell of the plant, thereby turning a petal blue via synthesis from glutamine to indigoidine;
   wherein the Sfp gene is a gene that encodes phosphopantetheinyl transferase having the amino acid sequence of SEQ ID NO:2; and
   the bpsA gene is a gene that encodes indigoidine synthetase having the amino acid sequence of SEQ ID NO: 4; and the plant is a rose.

12. The plant of claim 11, wherein the Sfp gene has the nucleotide sequence as shown in SEQ ID NO. 1.

13. The plant of claim 11, wherein the bpsA gene has the nucleotide sequence as shown in SEQ ID NO. 3.

* * * * *

SEQUENCE LISTING

<160> NUMBER OF SEQ ID NOS: 11

<210> SEQ ID NO 1
<211> LENGTH: 675
<212> TYPE: DNA
<213> ORGANISM: Artificial Sequence
<220> FEATURE:
<223> OTHER INFORMATION: Nucleotide sequence of Sfp gene with optimized
      gene codon preference

<400> SEQUENCE: 1
atgaagattt acagaattta tatggaccgc ccgctttcac aggaagaaaa tgaacggttc      60
atgtctttca tatcacctga aaacgggag aaatgccgga gattttatca taagaagat     120 gctcaccgca ccctgctggg agatgtgctc gttcgctcag tcataagcag gcagtatcag     180
ttggacaaat ccgatatccg ctttagcacg caggaatacg ggaagccgtg catcactgat     240
cttcccgacg ctcatttcaa catttctcac tccggccgct gggtcattgg tgcgtttgat     300
tcacagccga tcggcataga tatcgaaaaa acgaaaccga tcagccttga gatcgccaag     360
cgcttctttt caaaaacaga gtacagcgac ctttttagcaa aagacaagga cgagcgaaca     420
gactattttt atcatctatg gtcaatgaaa gagagcttta tcaaacagga aggcaaaggc     480
ttatcgcttc cgcttgattc ctttttcagtg cgcctgcatc aggacggaca agtatccatt     540
gagcttccgg acagccattc cccatgctat atcaaaacgt atgaggtcga tcccggctac     600
aaaatggctg tatgcgccgc acaccctgat ttccccgagg atatcacaat ggtgtcgtac     660
gaagagcttt tatag                                                     675

<210> SEQ ID NO 2
<211> LENGTH: 224
<212> TYPE: PRT
<213> ORGANISM: Bacillus subtilis

<400> SEQUENCE: 2

Met Lys Ile Tyr Arg Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
                20                  25                  30

Arg Arg Phe Tyr His Lys Glu Asp Ala His Arg Thr Leu Leu Gly Asp
            35                  40                  45

Val Leu Val Arg Ser Val Ile Ser Arg Gln Tyr Gln Leu Asp Lys Ser
        50                  55                  60

Asp Ile Arg Phe Ser Thr Gln Glu Tyr Gly Lys Pro Cys Ile Thr Asp
65                  70                  75                  80

Leu Pro Asp Ala His Phe Asn Ile Ser His Ser Gly Arg Trp Val Ile
                85                  90                  95

```
Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Arg Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 3
<211> LENGTH: 3852
<212> TYPE: DNA
<213> ORGANISM: Artificial Sequence
<220> FEATURE:
<223> OTHER INFORMATION: Nucleotide sequence of bpsA gene with
      optimized gene codon preference

<400> SEQUENCE: 3
```

| | | | | | |
|---|---|---|---|---|---|
| atgacccttc | aagaaaccag | cgttctggaa | ccgaccctgc | gcggaacgac | cacccctgccg 60 |
| gatctgctgg | caaaacgggt | tgcagaacat | ccggaagcaa | ccgcagttgc | atatcgcgat 120 |
| gaaaaactga | cctatcgtga | actggcaagc | cgtagcagcg | cactggcaga | atatctgcgt 180 |
| catctgggtg | ttagcaccga | tgattgtgtt | ggtctgtttg | ttgaaccgag | cattgatctg 240 |
| atggttggtg | catgggggtat | tctgagcgca | ggtgcagcat | atctgccgct | gagcccggaa 300 |
| tatccggaag | atcgcctgcg | ctatatgatt | gaaaatagcc | aggcaaaaat | tattctggca 360 |
| cagcagcgcc | tggttacccg | cctgcgcgaa | ctggcaccgc | aggatgttcg | tgttgttacc 420 |
| ctgcgcgaaa | gcgaagcatt | tgttctgccg | gaaggtcagg | ttgcaccggc | aattgaaggt 480 |
| gcacgtccgg | atagcctggc | ttatgttatc | tataccagcg | gtagcaccgg | taaaccgaaa 540 |
| ggtgttatga | ttgaacatca | tagcattgtt | agccagctgg | gttggctgcg | cgaaacctat 600 |
| ggtattgatc | gtagcaaaac | cattttacag | aaaaccccga | tgagctttga | tgcagcacag 660 |
| tgggaaattc | tgagcccggc | aaatggtgca | accgttgtta | tgggtgcacc | gggtgtttat 720 |
| gcagatccgg | aaggtctgat | tgaaaccatt | gttaaatatg | gttgttaccac | cctccagtgt 780 |
| gttccgaccc | tgctgcaagg | tctgctggat | accgaaaaat | tccggaatg | taccagcttg 840 |
| cagcagattt | ttagcggtgg | tgaagcactg | agccgcctgc | tggcaattca | gaccacccag 900 |
| gaaatgccgg | tcgcgcact | gattaatgtt | tatggtccga | ccgaatgtac | cattaatagc 960 |
| agcagctatg | cagttgatcc | ggcagaactg | ggtgaagcac | gcagagcat | agcattggt 1020 |
| gcaccggttg | cagataccga | atatcatatt | ctgggtaaag | aggacctgaa | accggttggt 1080 |
| gttggtgaaa | ttggtgaact | gtatattggt | ggtggtcagc | tggcacgcgg | ttatctgcat 1140 |
| cgcccggatc | tgaccgcaga | acgctttctg | gaaattgaag | ttaccgaagg | tgcaggtccg 1200 |
| gttcgcctgt | acaagaccgg | cgacctgggt | cagtggaatc | cggatggaac | cgttcagttt 1260 |
| gcaggtcgcg | cagataatca | ggttaaactg | cgcggttatc | gtgttgaact | ggatgaaatt 1320 |

-continued

```
agcctggcaa ttgaaaatca tgattgggtt cgtaatgcag cagttattgt taaaaatgat   1380
ggtcgtaccg gttttcagaa tctgattgca tgtgttgaac tgagcgaaaa agaagcagca   1440
ctgatggatc agggtaatca tggtagccat catgcaagca aaaaatccaa attgcaggtt   1500
aaagcacagc tgagcaatcc gggtctgcgc gatgatgcgg atctggcagc cagagttgct   1560
tacgatctgc cgggtgcaga accgaccccg gaacagcgta gccgtgtttt tgcaaggaaa   1620
acctatcgct tttatgaagg tggtgcagtt accgaagccg acctgctggc actgctgggt   1680
ggtcaggttc cggcagcata tagccgtaaa gcagctgacc tggcaccggc agaactgggt   1740
cagattctgc gttggtttgg tcagtatctg agcgaagaac gcctgctgcc gaaatatggt   1800
tatgcatcgc caggtgcact gtatgcaacc cagctgtatt ttgaactgga aggtgttggt   1860
ggtctgcaac cgggttatta ttattatcag ccgcagcgcc atcagctggt tctgattagc   1920
gaaaaagcag caaccggtcg tccgaccgca catattcatt ttattggtaa acgcggtggt   1980
attgaaccgg tttacaaaaa caatattcag gaagttctgg aaattgaaac cggtcatatt   2040
gttggtctgt ttgaacaggt tctgccggcc tacggtctgg atattcgtga tctggcctac   2100
gaaccggcag ttcgcgatct gctggatgtt ccggaagaag attttttatct gggaacgttt   2160 gaactggttc cgcataccgg tcgtcgtgaa gatcatgcag aagtttatgt tcagactcac   2220
ggtagcaaag ttgcaaatct gccggaaggt cagtatcgct atgcagatgg cacgctgacc   2280
cgctttagcg atgatattgt tctgaaaaaa caggttattg caattaatca gagcgtttat   2340
caggcagcct cctttggtat tagcgttatt agccgcgcac cggaagagtg gatgcattat   2400
gttaccctgg gcaagaaact ccagcatctg atgatgaatg gtctgggtct gggttttatg   2460
agcagcggtt atagcagcaa aaccggtaat ccgctgccgg caagccgtcg cattgatagc   2520
gttctacaag caaatggtgt tgaaagcggt ccgagctatt tctttgttgg tggtcgtgtt   2580
agcgatgaac agctgggtca tgaaggtatg cgtgaagata gcgttcacat gcgcggtccg   2640
gcagaactga ttcgcgatga tctggttagc tttctgccgg attatatgat tccgaatcgt   2700
gttgttgttt ttgaacgcct gccgctgagc gcaaatggga agattgatgc aaaagcactg   2760
gcagcaagcg atcaggttaa tgcagaactg gttgaacgcc gtttgttgc accgcgtacc   2820 gaaaccgaaa agaaattgc agaagtttgg gcaaaaagcc tgcgtcgcga agcgttagc   2880 gttcaggatg atttctttga aagcggtggt aatagcctga ttgcagttgg tctgattcgc   2940
gaactgaata gccgcctggg tgttagcctg ccgctacaga gcgttctgga aagcccgacc   3000
gttgaaaaac tgagccgtcg cctggaacgc gaagttcac aggaaagcag ccgcctggtt   3060
cgccttcacg cagaaaccgg taaagatcgt ccggttctgt gttggccggg tctgggtggt   3120
tatccgatga atctgcgtac cctggcaggt gaaattggtc tgggtcgtag cttttatggt   3180
attcaggcac atggtattaa cgaaggtgaa gcaccgtatg caaccattac gaaatggca   3240 aaagcagata ttgaagcaat taagaattg caaccgaaag gtccgtatac cctgtggggt   3300
tatagctttg gtgcgcgtgt tgcatttgaa accgcatatc agctggaaca ggcaggtgaa   3360
aaagttgata atctgtttct gattgcaccg ggtagcccga ccgttcgcgc agaaaatggt   3420
aaagtttatg tcgcgaagc cagttttgca atcgcgcat ataccaccat tctgtttagc   3480
gtttttaccg gaactattag cggtccggat ctggaaaaat gtctggaaag cgcaaccgat   3540
gaagaaagtt ttgcaggttt tattagcgaa ctgaaaggta ttgatgttga tctggcaaaa   3600
cgtattatta gcgttgttgg tcagacctat gaatttgaat atagctttcg cgaactggca   3660
```

```
gaacgtaccc tggcagcacc ggttaccatt tttaaagcac gcggcgatga ttatagcttt    3720
attgaaaata gcaatggtta tagcgcagaa ccgccgaccg ttattgatct ggatgcagat    3780
cattatagcc tgctgcgtac cccggatatt ggtgaactgg ttaaacatat tcgctatctg    3840
ctgggtgaat aa                                                        3852
```

<210> SEQ ID NO 4
<211> LENGTH: 1283
<212> TYPE: PRT
<213> ORGANISM: Streptomyces lavendulae

<400> SEQUENCE: 4

```
Met Thr Leu Gln Glu Thr Ser Val Leu Glu Pro Thr Leu Arg Gly Thr
1               5                   10                  15

Thr Thr Leu Pro Asp Leu Leu Ala Lys Arg Val Ala Glu His Pro Glu
            20                  25                  30

Ala Thr Ala Val Ala Tyr Arg Asp Glu Lys Leu Thr Tyr Arg Glu Leu
        35                  40                  45

Ala Ser Arg Ser Ser Ala Leu Ala Glu Tyr Leu Arg His Leu Gly Val
    50                  55                  60

Ser Thr Asp Asp Cys Val Gly Leu Phe Val Glu Pro Ser Ile Asp Leu
65                  70                  75                  80

Met Val Gly Ala Trp Gly Ile Leu Ser Ala Gly Ala Ala Tyr Leu Pro
                85                  90                  95

Leu Ser Pro Glu Tyr Pro Glu Asp Arg Leu Arg Tyr Met Ile Glu Asn
            100                 105                 110

Ser Gln Ala Lys Ile Ile Leu Ala Gln Gln Arg Leu Val Thr Arg Leu
        115                 120                 125

Arg Glu Leu Ala Pro Gln Asp Val Arg Val Val Thr Leu Arg Glu Ser
    130                 135                 140

Glu Ala Phe Val Leu Pro Glu Gly Gln Val Ala Pro Ala Ile Glu Gly
145                 150                 155                 160

Ala Arg Pro Asp Ser Leu Ala Tyr Val Ile Tyr Thr Ser Gly Ser Thr
                165                 170                 175

Gly Lys Pro Lys Gly Val Met Ile Glu His His Ser Ile Val Ser Gln
            180                 185                 190

Leu Gly Trp Leu Arg Glu Thr Tyr Gly Ile Asp Arg Ser Lys Thr Ile
        195                 200                 205

Leu Gln Lys Thr Pro Met Ser Phe Asp Ala Ala Gln Trp Glu Ile Leu
    210                 215                 220

Ser Pro Ala Asn Gly Ala Thr Val Val Met Gly Ala Pro Gly Val Tyr
225                 230                 235                 240

Ala Asp Pro Glu Gly Leu Ile Glu Thr Ile Val Lys Tyr Gly Val Thr
                245                 250                 255

Thr Leu Gln Cys Val Pro Thr Leu Leu Gln Gly Leu Leu Asp Thr Glu
            260                 265                 270

Lys Phe Pro Glu Cys Thr Ser Leu Gln Gln Ile Phe Ser Gly Gly Glu
        275                 280                 285

Ala Leu Ser Arg Leu Leu Ala Ile Gln Thr Thr Gln Glu Met Pro Gly
    290                 295                 300

Arg Ala Leu Ile Asn Val Tyr Gly Pro Thr Glu Cys Thr Ile Asn Ser
305                 310                 315                 320

Ser Ser Tyr Ala Val Asp Pro Glu Leu Gly Glu Ala Pro Gln Ser
                325                 330                 335
```

```
Ile Ser Ile Gly Ala Pro Val Ala Asp Thr Glu Tyr His Ile Leu Gly
                340                 345                 350

Lys Glu Asp Leu Lys Pro Val Gly Val Gly Glu Ile Gly Glu Leu Tyr
            355                 360                 365

Ile Gly Gly Gly Gln Leu Ala Arg Gly Tyr Leu His Arg Pro Asp Leu
        370                 375                 380

Thr Ala Glu Arg Phe Leu Glu Ile Glu Val Thr Glu Gly Ala Gly Pro
385                 390                 395                 400

Val Arg Leu Tyr Lys Thr Gly Asp Leu Gly Gln Trp Asn Pro Asp Gly
                405                 410                 415

Thr Val Gln Phe Ala Gly Arg Ala Asp Asn Gln Val Lys Leu Arg Gly
            420                 425                 430

Tyr Arg Val Glu Leu Asp Glu Ile Ser Leu Ala Ile Glu Asn His Asp
        435                 440                 445

Trp Val Arg Asn Ala Ala Val Ile Val Lys Asn Asp Gly Arg Thr Gly
        450                 455                 460

Phe Gln Asn Leu Ile Ala Cys Val Glu Leu Ser Glu Lys Glu Ala Ala
465                 470                 475                 480

Leu Met Asp Gln Gly Asn His Gly Ser His His Ala Ser Lys Lys Ser
                485                 490                 495

Lys Leu Gln Val Lys Ala Gln Leu Ser Asn Pro Gly Leu Arg Asp Asp
            500                 505                 510

Ala Asp Leu Ala Ala Arg Val Ala Tyr Asp Leu Pro Gly Ala Glu Pro
        515                 520                 525

Thr Pro Glu Gln Arg Ser Arg Val Phe Ala Arg Lys Thr Tyr Arg Phe
530                 535                 540

Tyr Glu Gly Gly Ala Val Thr Glu Ala Asp Leu Leu Ala Leu Leu Gly
545                 550                 555                 560

Gly Gln Val Pro Ala Ala Tyr Ser Arg Lys Ala Ala Asp Leu Ala Pro
                565                 570                 575

Ala Glu Leu Gly Gln Ile Leu Arg Trp Phe Gly Gln Tyr Leu Ser Glu
            580                 585                 590

Glu Arg Leu Leu Pro Lys Tyr Gly Tyr Ala Ser Pro Gly Ala Leu Tyr
        595                 600                 605

Ala Thr Gln Leu Tyr Phe Glu Leu Glu Gly Val Gly Gly Leu Gln Pro
        610                 615                 620

Gly Tyr Tyr Tyr Tyr Gln Pro Gln Arg His Gln Leu Val Leu Ile Ser
625                 630                 635                 640

Glu Lys Ala Ala Thr Gly Arg Pro Thr Ala His Ile His Phe Ile Gly
                645                 650                 655

Lys Arg Gly Gly Ile Glu Pro Val Tyr Lys Asn Asn Ile Gln Glu Val
            660                 665                 670

Leu Glu Ile Glu Thr Gly His Ile Val Gly Leu Phe Glu Gln Val Leu
        675                 680                 685

Pro Ala Tyr Gly Leu Asp Ile Arg Asp Leu Ala Tyr Glu Pro Ala Val
        690                 695                 700

Arg Asp Leu Leu Asp Val Pro Glu Glu Asp Phe Tyr Leu Gly Thr Phe
705                 710                 715                 720

Glu Leu Val Pro His Thr Gly Arg Arg Glu Asp His Ala Glu Val Tyr
                725                 730                 735

Val Gln Thr His Gly Ser Lys Val Ala Asn Leu Pro Glu Gly Gln Tyr
            740                 745                 750

Arg Tyr Ala Asp Gly Thr Leu Thr Arg Phe Ser Asp Asp Ile Val Leu
```

```
                755                 760                 765
Lys Lys Gln Val Ile Ala Ile Asn Gln Ser Val Tyr Gln Ala Ala Ser
    770                 775                 780

Phe Gly Ile Ser Val Ile Ser Arg Ala Pro Glu Glu Trp Met His Tyr
785                 790                 795                 800

Val Thr Leu Gly Lys Leu Gln His Leu Met Met Asn Gly Leu Gly
                805                 810                 815

Leu Gly Phe Met Ser Ser Gly Tyr Ser Ser Lys Thr Gly Asn Pro Leu
        820                 825                 830

Pro Ala Ser Arg Arg Ile Asp Ser Val Leu Gln Ala Asn Gly Val Glu
            835                 840                 845

Ser Gly Pro Ser Tyr Phe Phe Val Gly Gly Arg Val Ser Asp Glu Gln
850                 855                 860

Leu Gly His Glu Gly Met Arg Glu Asp Ser Val His Met Arg Gly Pro
865                 870                 875                 880

Ala Glu Leu Ile Arg Asp Asp Leu Val Ser Phe Leu Pro Asp Tyr Met
                885                 890                 895

Ile Pro Asn Arg Val Val Val Phe Glu Arg Leu Pro Leu Ser Ala Asn
            900                 905                 910

Gly Lys Ile Asp Ala Lys Ala Leu Ala Ala Ser Asp Gln Val Asn Ala
        915                 920                 925

Glu Leu Val Glu Arg Pro Phe Val Ala Pro Arg Thr Glu Thr Glu Lys
    930                 935                 940

Glu Ile Ala Glu Val Trp Ala Lys Ser Leu Arg Arg Glu Ser Val Ser
945                 950                 955                 960

Val Gln Asp Asp Phe Phe Glu Ser Gly Gly Asn Ser Leu Ile Ala Val
                965                 970                 975

Gly Leu Ile Arg Glu Leu Asn Ser Arg Leu Gly Val Ser Leu Pro Leu
            980                 985                 990

Gln Ser Val Leu Glu Ser Pro Thr Val Glu Lys Leu Ser Arg Arg Leu
        995                 1000                1005

Glu Arg Glu Val Ala Gln Glu Ser Ser Arg Leu Val Arg Leu His
    1010                1015                1020

Ala Glu Thr Gly Lys Asp Arg Pro Val Leu Cys Trp Pro Gly Leu
    1025                1030                1035

Gly Gly Tyr Pro Met Asn Leu Arg Thr Leu Ala Gly Glu Ile Gly
    1040                1045                1050

Leu Gly Arg Ser Phe Tyr Gly Ile Gln Ala His Gly Ile Asn Glu
    1055                1060                1065

Gly Glu Ala Pro Tyr Ala Thr Ile Thr Glu Met Ala Lys Ala Asp
    1070                1075                1080

Ile Glu Ala Ile Lys Glu Leu Gln Pro Lys Gly Pro Tyr Thr Leu
    1085                1090                1095

Trp Gly Tyr Ser Phe Gly Ala Arg Val Ala Phe Glu Thr Ala Tyr
    1100                1105                1110

Gln Leu Glu Gln Ala Gly Glu Lys Val Asp Asn Leu Phe Leu Ile
    1115                1120                1125

Ala Pro Gly Ser Pro Thr Val Arg Ala Glu Asn Gly Lys Val Tyr
    1130                1135                1140

Gly Arg Glu Ala Ser Phe Ala Asn Arg Ala Tyr Thr Thr Ile Leu
    1145                1150                1155

Phe Ser Val Phe Thr Gly Thr Ile Ser Gly Pro Asp Leu Glu Lys
    1160                1165                1170
```

```
Cys Leu Glu Ser Ala Thr Asp Glu Ser Phe Ala Gly Phe Ile
    1175                1180                1185

Ser Glu Leu Lys Gly Ile Asp Val Asp Leu Ala Lys Arg Ile Ile
    1190                1195                1200

Ser Val Val Gly Gln Thr Tyr Glu Phe Glu Tyr Ser Phe Arg Glu
    1205                1210                1215

Leu Ala Glu Arg Thr Leu Ala Ala Pro Val Thr Ile Phe Lys Ala
    1220                1225                1230

Arg Gly Asp Asp Tyr Ser Phe Ile Glu Asn Ser Asn Gly Tyr Ser
    1235                1240                1245

Ala Glu Pro Pro Thr Val Ile Asp Leu Asp Ala Asp His Tyr Ser
    1250                1255                1260

Leu Leu Arg Thr Pro Asp Ile Gly Glu Leu Val Lys His Ile Arg
    1265                1270                1275

Tyr Leu Leu Gly Glu
    1280

<210> SEQ ID NO 5
<211> LENGTH: 2934
<212> TYPE: DNA
<213> ORGANISM: Rosa hybrida

<400> SEQUENCE: 5
aagcttcagc aagagttgaa gaaatagggc cagagccatc catgtgcttt gatgaatctg      60
atgggataca aaatgtgaaa gattcacttg ctgatttatc cagaatttct tcatatagtg     120
aggagaatgt tgaaagatct aatgatgagc actctgttaa actagacgga attcatgtgc     180
agcacgagtg tcatgagggc agtgaagaag acaaacctga tggtaagagc ggtgagaatg     240
cagttgatct ggctaatcat ggcatggctc gaactgattt ttgtcagata acagaagaga     300
ttgagaatgg agtagtcatc actgagatga gcaacattgc caaccctgat aaaactgata     360
ttccaaacgg ggtgcctcaa aatgagactg atgatggatt taataacact caggatgatg     420
ctaatacaaa ggaagtgaca gaagagaatt ctgacagacg tgcgaaggaa gtgacagaag     480
agaattctga caaagatgtt ttgaagaata tccttgaatt ctcacgtgct tcttctgtgg     540
tggattttga attccagtg ttggatgtga aatttacttc tcttgaaagt tgcagtgcca      600
cttgttctct tgcagccctt tgtctgaatc gccggaatc aatgactgaa gcaccttgtg      660
tgaggcaaat tgatgatgtg cccccggttg gtgaggagtc tagcttgatt ttggtggaag     720
atcgggagcc ggttggtcct actcctgatg gtaattttc tgtggatatg gattactata      780
gtgtagcaga acctttgagc acatgggatg cgaatctgca gtgtgaaaca tcaaatagcc     840
atgagacttt tgctgcaagt ctcatttgat agcttctgtg ttaataactt tgttagtctg     900
tacataaatt tgtctagaca agaattggtc gtgtactatc gtgtgttttt gccgtgcttt     960
agtactcatg aaccaattca gagaaaactg gctgcatatt tgaggagtc tctgaattct     1020
tcaatgctca actggtatgc atgtaggtgg catatcactt cagggattct tctattcttt    1080
aactttacgc atcttgacat tttgtatata caaaatcag gtctattggg tgaaagtaat     1140
tggctagaat ggaaagctct acggttttac cgcaggtcaa ttttcatagc tccacaagtg    1200
aattgaaaat gctcataggc tttatgtttg tcctccacct ctggcgacga tgtttgttgg    1260
ggagttaact caaacctacc accaaactcg aacccatctt ccataattta taatacaaat    1320
ttgcgatcat ttgttcatcc aattattgtg acactcggct accacccaaa atatcggtca    1380
```

-continued

```
cagacccaaa cgtattgtca caacaaatcg tgtctctcgc attaaacaca gctagaaaga    1440
agagttgaac ccacaattcg agcacccact acctatgtac gaagtcatga gttcgagtca    1500 ccatagggt  agaagtgaaa tcatttgatc atctttaaag aaataaaagg aagagttgaa    1560
cccacaattg gctcttgtcc caaaaagaac taatagttca gtgcaccgac gtgtatttgc    1620
accgacataa atggattgtt agattatatt aaatacactc ttaggttatt aataaaaata    1680
ttaattataa atatcaaaag ttgagatcat cttataaatg ttgggtcagt tacaccgtcg    1740
gtgcatagaa taatttccaa actatataat agccttcatt ttctgattta gctcatggga    1800
catgattgct ataaataatt gtactcgtag aggcatactt gtgtcttttt atacagttgt    1860
actgaagctc agaaaagttt atgaaggtga gaactgagaa gggcaaggca tttggtagtt    1920
gaggtatatg agagcatgaa ccccatgcat tgcagctacc acctctcttt tttccttctt    1980
cccatacaaa taaaccaac  tcttctcacc taagtctatc atctttattt atggcagctc    2040
ttgcttaatt agctcatcta tattatatta tttatctata atatgtgtca ctctgtctac    2100
ctaccagccc aaaataaaac tgataatagt caatttgatg atatttttg  ttttttgttt    2160 tgttttgtct tttttgtatt gatttttta  aaattaaaat gacttcattt tttgtttttg    2220 ttttttttc  tatttttttt tatagaaaaa ttggcaaact ttcattatct gttattgatg    2280
acaattaagc cattaaaacc tataattaat tatctttcaa ttcgagtaaa tttaaaacgg    2340
tgtaaaatta aaatatgatc gtattcttaa atgaataaaa ctcacttaat aatagtaata    2400
cttgaatcac atctacgaac atagattctt ttcatccagt ctaaccatgt ttgaatatat    2460
agagtttgat tatggttatg tctttgtcca cattttggtt tgtaaataaa tgtgcaacgg    2520
aggtatggta ctgttgctct atcaaattca gtttgaatt  aaagaaaaa  aaaaaagacg    2580 atattttgtg cgctttgttt ggtaggtaaa acgagagaac aaacgcattc caaatcatgc    2640
ggattttgat cggcaacaca caccacaaaa aaccgtacac gatgcacgtg ccatttgccg    2700
ggggtttcta acaaggtaat tgggcaggca cgtgatcccc cagctaccca cctctcgctt    2760
cccttctcaa actcctttc  catgtatata taacaccct  tttctcagac cattatattc    2820
taacattttt gctttgctat tgtaacgcaa caaaaactgc tcattccatc cttgttcctc    2880 cccatttga  tcttctctcg accttctcc  gagatgggta ccgagctcga attc          2934
```

<210> SEQ ID NO 6
<211> LENGTH: 1183
<212> TYPE: DNA
<213> ORGANISM: Rosa hybrida

<400> SEQUENCE: 6

```
cgatggactc cagagcggcc gcggggtggg tttccccacc acgtgtcttt acgaccctcc      60
aatcagaaga gaggaaattt tcaatctttt ccaaaattgc ccctgctccc tgaagtgcaa     120
tacccaaaac actccctgc  tgggcattga ttggccctcc ccaccacgtg tccgtgcggg     180
tgccctacgc aagattctct cctcttcctc ctctatatcc catcaatcat tcacaggtaa     240
aagaattaat gtatatcttt gataaaataa atgagtaaaa actggacggt tgatggaccc     300
tgaatcaaat gagtgattcc catggttct  ctttactttt gcttcaggtc caatacaaaa     360
tgtattatac cacttacatt tccttgtaat aataactaaa gtcatataca ttaaaaattg     420
aagccaagtt ttggaaatta gtataatgga ggaaagatcg ttttccctt  tataaatacc     480 ttctctgagt cccccttgct ttcatttttc tgcatatctt cttgtttaga ttgtggaaaa     540 gaaagaagt  ctaagaaaaa acccaaaagg tagaaacctc tctgtttctt tcatcatctc     600
```

| | | | |
|---|---|---|---|
| catcttctct | tgttttctt | atctgggtat | tgatcaaaat actcaaaaca ccatctggta | 660 |
| atccaatctt | cagtgcctca | cttttttagt | ccaattcatg tttttgactt ttgagtactc | 720 |
| cacagctagc | tagatcagca | actgcttgat | gtttgctgtc aaagaaccca aaaagcaatg | 780 |
| aacttaaaat | ttttagtcc | atcagttcac | aatttctttt agtccaattc atgtttttag | 840 |
| ctccacagct | agatcagcaa | ctgtactttg | atgtttgttg tcaaagaacc caaagtgcaa | 900 |
| tgaacttatt | aactctcagt | ccatcagttc | gcaattctt gagctagtta gctagttgta | 960 |
| gtgtaacacc | acgctttct | tgatcaaagc | tagataggg agattagtac tatttagaaa | 1020 |
| ccgtcttttg | attttctaat | tgtacataa | agtttgatcc ttttttgctt gattgatgat | 1080 |
| tctcattgta | cattggcctt | tttttttct | ttcccctact tgattgatga ctctcattgt | 1140 |
| ggaaaagaaa | agaagtctaa | gaaaaaaccc | aaaagctgca act | 1183 |

<210> SEQ ID NO 7
<211> LENGTH: 4491
<212> TYPE: DNA
<213> ORGANISM: Artificial Sequence
<220> FEATURE:
<223> OTHER INFORMATION: Synthetic fragment for constructing plasmid pBI121-CHS-RhAG

<400> SEQUENCE: 7

| | | | |
|---|---|---|---|
| tgaaggcggg | aaacgacaat | ctgatcatga | gcggagaatt aagggagtca cgttatgacc | 60 |
| cccgccgatg | acgcgggaca | agccgtttta | cgtttggctc gaggataatt tatttgaaaa | 120 |
| ttcataagaa | aagcaaacgt | tacatgaatt | gatgaaacaa tacaaagaca gataaagcca | 180 |
| cgcacattta | ggatattggc | cgagattact | gaatattgag taagatcacg gaatttctga | 240 |
| caggagcatg | tcttcaattc | agcccaaatg | gcagttgaaa tactcaaacc gccccatatg | 300 |
| caggagcgga | tcattcattg | tttgtttggt | tgcctttgcc aacatgggag tccaagggat | 360 |
| ccgaattcga | gctcggtacc | catctcggag | aagggtcgag agaagatcaa atgggggagg | 420 |
| aacaaggatg | gaatgagcag | ttttgttgc | gttacaatag caaagcaaaa atgttagaat | 480 |
| ataatggtct | gagaaaaggg | gttgtatata | tacatggaaa aggagtttga gaagggaagc | 540 |
| gagaggtggg | tagctggggg | atcacgtgcc | tgcccaatta ccttgttaga acccccggc | 600 |
| aaatggcacg | tgcatcgtgt | acggtttttt | gtggtgtgtg ttgccgatca aaatccgcat | 660 |
| gatttggaat | gcgtttgttc | tctcgtttta | cctaccaaac aaagcgcaca aaatatcgtc | 720 |
| tttttttttt | tcttttaatt | caaacttgaa | tttgatagag caacagtacc atacctccgt | 780 |
| tgcacattta | tttacaaacc | aaaatgtgga | caaagacata accataatca aactctatat | 840 |
| attcaaacat | ggttagactg | gatgaaaaga | atctatgttc gtagatgtga ttcaagtatt | 900 |
| actattatta | agtgagtttt | attcatttaa | gaatacgatc atattttaat tttacaccgt | 960 |
| tttaaattta | ctcgaattga | agataatta | attataggtt ttaatggctt aattgtcatc | 1020 |
| aataacagat | aatgaaagtt | tgccaatttt | tctataaaa aaaatagaaa aaaaaacaaa | 1080 |
| aacaaaaaat | gaagtcattt | taattttaaa | aaatcaata caaaaagac aaaacaaaac | 1140 |
| aaaaaacaaa | aaatatcatc | aaattgacta | ttatcagttt tattttgggc tggtaggtag | 1200 |
| acagagtgac | acatattata | gataaataat | ataatataga tgagctaatt aagcaagagc | 1260 |
| tgccataaat | aaagatgata | gacttaggtg | agaagagttg gttttatttg tatgggaaga | 1320 |
| aggaaaaaag | agaggtggta | gctgcaatgc | atggggttca tgctctcata tacctcaact | 1380 |
| accaaatgcc | ttgcccttct | cagttctcac | cttcataaac ttttctgagc ttcagtacaa | 1440 |

```
ctgtataaaa agacacaagt atgcctctac gagtacaatt atttatagca atcatgtccc   1500
atgagctaaa tcagaaaatg aaggctatta tatagtttgg aaattattct atgcaccgac   1560
ggtgtaactg acccaacatt tataagatga tctcaacttt tgatatttat aattaatatt   1620
tttattaata acctaagagt gtatttaata taatctaaca atccatttat gtcggtgcaa   1680
atacacgtcg gtgcactgaa ctattagttc ttttgggac aagagccaat tgtgggttca    1740
actcttcctt ttatttcttt aaagatgatc aaatgattc acttctaccc ctatggtgac    1800
tcgaactcat gacttcgtac ataggtagtg ggtgctcgaa ttgtgggttc aactcttctt   1860
tctagctgtg tttaatgcga gagacacgat ttgttgtgac aatacgtttg ggtctgtgac   1920
cgatattttg ggtggtagcc gagtgtcaca ataattggat gaacaaatga tcgcaaattt   1980
gtattataaa ttatggaaga tgggttcgag tttggtggta ggtttgagtt aactccccaa   2040
caaacatcgt cgccagaggt ggaggacaaa cataaagcct atgagcattt tcaattcact   2100
tgtggagcta tgaaaattga cctgcggtaa aaccgtagag cttttccattc tagccaatta   2160 cttttcaccca atagacctga ttttgttata tacaaaatgt caagatgcgt aaagttaaag   2220
aatagaagaa tccctgaagt gatatgccac ctacatgcat accagttgag cattgaagaa   2280
ttcagagact cctcaaaata tgcagccagt tttctctgaa ttggttcatg agtactaaag   2340
cacggcaaaa acacacgata gtacacgacc aattcttgtc tagacaaatt tatgtacaga   2400
ctaacaaagt tattaacaca gaagctatca aatgagactt gcagcaaaag tctcatggct   2460
atttgatgtt tcacactgca gattcgcatc ccatgtgctc aaaggttctg ctacactata   2520
gtaatccata tccacagaaa aattaccatc aggagtagga ccaaccggct cccgatcttc   2580
caccaaaatc aagctagact cctcaccaac cggggggcaca tcatcaattt gcctcacaca   2640
aggtgcttca gtcattgatt ccggcgattc agacaaaagg gctgcaagag aacaagtggc   2700
actgcaactt tcaagagaag taaatttcac atccaacact ggaatttcaa aatccaccac   2760
agaagaagca cgtgagaatt caaggatatt cttcaaaaca tctttgtcag aattctcttc   2820
tgtcacttcc ttcgcacgtc tgtcagaatt ctcttctgtc acttcctttg tattagcatc   2880
atcctgagtg ttattaaatc catcatcagt ctcattttga ggcaccccgt ttggaatatc   2940
agttttatca gggttggcaa tgttgctcat ctcagtgatg actactccat tctcaatctc   3000
ttctgttatc tgacaaaaat cagttcgagc catgccatga ttagccagat caactgcatt   3060
ctcaccgctc ttaccatcag gtttgtcttc ttcactgccc tcatgacact cgtgctgcac   3120
atgaattccg tctagtttaa cagagtgctc atcattagat cttcaacat tctcctcact    3180 atatgaagaa attctggata aatcagcaag tgaatctttc acattttgta tcccatcaga   3240
ttcatcaaag cacatggatg gctctgtccc tatttcttca actcttgctg aagcttcccg   3300
ggcgatggac tccagagcgg ccgcggggtg ggtttcccca ccacgtgtct ttacgaccct   3360
ccaatcagaa gagaggaaat tttcaatctt ttccaaaatt gccctgctc cctgaagtgc     3420 aatacccaaa acactcccct gctgggcatt gattggccct cccaccacg tgtccgtgcg    3480 ggtgccctac gcaagattct ctcctcttcc tcctctatat cccatcaatc attcacaggt   3540
aaaagaatta atgtatatct ttgataaaat aaatgagtaa aaactggacg gttgatggac   3600
cctgaatcaa atgagtgatt cccatggttt ctctttactt ttgcttcagg tccaatacaa   3660
aatgtattat accacttaca tttccttgta ataataacta aagtcatata cattaaaaat   3720
tgaagccaag ttttggaaat tagtataatg gaggaaagat cgttttccc tttataaata    3780
```

-continued

| | |
|---|---|
| ccttctctga gtcccccttg ctttcatttt tctgcatatc ttcttgttta gattgtggaa | 3840 |
| aagaaaagaa gtctaagaaa aaacccaaaa ggtagaaacc tctctgtttc tttcatcatc | 3900 |
| tccatcttct ctttgttttc ttatctgggt attgatcaaa atactcaaaa caccatctgg | 3960 |
| taatccaatc ttcagtgcct cactttttta gtccaattca tgtttttgac ttttgagtac | 4020 |
| tccacagcta gctagatcag caactgcttg atgtttgctg tcaaagaacc caaaaagcaa | 4080 |
| tgaacttaaa attttttagt ccatcagttc acaatttctt ttagtccaat tcatgttttt | 4140 |
| agctccacag ctagatcagc aactgtactt tgatgtttgt tgtcaaagaa cccaaagtgc | 4200 |
| aatgaactta ttaactctca gtccatcagt tcgcaatttc ttgagctagt tagctagttg | 4260 |
| tagtgtaaca ccacgctttt cttgatcaaa gctagatagg ggagattagt actatttaga | 4320 |
| aaccgtcttt tgattttcta atttgtacat aaagtttgat ccttttttgc ttgattgatg | 4380 |
| attctcattg tacattggcc tttttttttt ctttccccta cttgattgat gactctcatt | 4440 |
| gtggaaaaga aagaagtct aagaaaaaac ccaaaagctg caactactag t | 4491 |

<210> SEQ ID NO 8
<211> LENGTH: 48
<212> TYPE: DNA
<213> ORGANISM: Artificial Sequence
<220> FEATURE:
<223> OTHER INFORMATION: Primer BpsA-FG

<400> SEQUENCE: 8
agaaaaaacc caaaagctgc aactaatgac ccttcaagaa accagcgt            48

<210> SEQ ID NO 9
<211> LENGTH: 55
<212> TYPE: DNA
<213> ORGANISM: Artificial Sequence
<220> FEATURE:
<223> OTHER INFORMATION: Primer BpsA-RG

<400> SEQUENCE: 9
ttgaacgatc ggggaaattc gagctcatta ttcacccagc agatagcgaa tatgt      55

<210> SEQ ID NO 10
<211> LENGTH: 57
<212> TYPE: DNA
<213> ORGANISM: Artificial Sequence
<220> FEATURE:
<223> OTHER INFORMATION: Primer Sfp-FG

<400> SEQUENCE: 10
gagatgggta ccgagctcga attcgatgaa gatttacaga atttatatgg accgccc    57

<210> SEQ ID NO 11
<211> LENGTH: 55
<212> TYPE: DNA
<213> ORGANISM: Artificial Sequence
<220> FEATURE:
<223> OTHER INFORMATION: Primer Sfp-RG

<400> SEQUENCE: 11
cctttgccaa catgggagtc caaggctata aaagctcttc gtacgacacc attgt       55